United States Patent
Justin et al.

(10) Patent No.: US 8,241,367 B2
(45) Date of Patent: *Aug. 14, 2012

(54) MODULAR BONE IMPLANT, TOOL, AND METHOD

(75) Inventors: Daniel F. Justin, Logan, UT (US); E. Marlowe Goble, Alta, WY (US); Thomas Wade Fallin, Hyde Park, UT (US); Nathan A. Hammond, Logan, UT (US); Daniel J. Triplett, West Jordan, UT (US); Robert A. Hodorek, Warsaw, IN (US); Daniel Gerbec, Logan, UT (US); Gordon Baker, Nibley, UT (US)

(73) Assignees: Zimmer, Inc., Warsaw, IN (US); Zimmer Technology, Inc., Warsaw, IN (US)

( * ) Notice: Subject to any disclaimer, the term of this patent is extended or adjusted under 35 U.S.C. 154(b) by 79 days.

This patent is subject to a terminal disclaimer.

(21) Appl. No.: 12/951,864

(22) Filed: Nov. 22, 2010

(65) Prior Publication Data

US 2011/0066249 A1  Mar. 17, 2011

Related U.S. Application Data

(63) Continuation of application No. 11/625,053, filed on Jan. 19, 2007, now Pat. No. 7,857,858, which is a continuation of application No. 10/369,331, filed on Feb. 18, 2003, now Pat. No. 7,182,786, which is a continuation-in-part of application No. 10/132,668, filed on Apr. 25, 2002, now abandoned.

(51) Int. Cl.
*A61F 2/38* (2006.01)
*A61F 2/46* (2006.01)

(52) U.S. Cl. .............. 623/20.34; 623/23.44; 623/23.46
(58) Field of Classification Search .... 623/20.14–20.34, 623/23.44–23.47
See application file for complete search history.

(56) References Cited

U.S. PATENT DOCUMENTS

| | | |
|---|---|---|
| 2,682,265 A | 6/1954 | Collison |
| 2,725,878 A | 12/1955 | Reiter |
| 2,785,673 A | 3/1957 | Anderson |
| 3,806,957 A | 4/1974 | Shersher |
| 3,848,272 A | 11/1974 | Noiles |
| 3,875,593 A | 4/1975 | Shersher |
| 3,906,550 A | 9/1975 | Rostoker et al. |
| 3,943,576 A | 3/1976 | Sivash |
| 3,987,499 A | 10/1976 | Scharbach et al. |
| 4,016,651 A | 4/1977 | Kawahara et al. |
| 4,051,559 A | 10/1977 | Pifferi |
| 4,086,701 A | 5/1978 | Kawahara et al. |
| 4,259,072 A | 3/1981 | Hirabayashi et al. |

(Continued)

FOREIGN PATENT DOCUMENTS

DE  3205577 A1  10/1982

(Continued)

OTHER PUBLICATIONS

The Office Action mailed Oct. 16, 2008 in related Australian application No. 2004200394.

(Continued)

*Primary Examiner* — David H Willse
*Assistant Examiner* — Javier Blanco
(74) *Attorney, Agent, or Firm* — Faegre Baker Daniels

(57) ABSTRACT

Modular bone implants, modes of assembly, and their method of use are presented.

12 Claims, 5 Drawing Sheets

U.S. PATENT DOCUMENTS

| | | | |
|---|---|---|---|
| 4,304,011 A | 12/1981 | Whelan, III | |
| 4,404,691 A | 9/1983 | Buning et al. | |
| 4,520,511 A | 6/1985 | Gianezio et al. | |
| 4,578,081 A | 3/1986 | Harder et al. | |
| 4,619,659 A | 10/1986 | Witzel | |
| 4,624,673 A | 11/1986 | Meyer | |
| 4,676,797 A | 6/1987 | Anapliotis et al. | |
| 4,714,471 A | 12/1987 | Brundei | |
| 4,790,854 A | 12/1988 | Harder et al. | |
| 4,822,366 A | 4/1989 | Bolesky | |
| 4,842,606 A | 6/1989 | Kranz et al. | |
| 4,846,839 A | 7/1989 | Noiles | |
| 4,851,007 A | 7/1989 | Gray | |
| 4,878,917 A | 11/1989 | Kranz et al. | |
| 4,908,032 A | 3/1990 | Keller | |
| 4,917,530 A | 4/1990 | Engelhardt et al. | |
| 4,919,678 A | 4/1990 | Kranz | |
| 4,936,853 A | 6/1990 | Fabian et al. | |
| 4,938,769 A | 7/1990 | Shaw | |
| 4,938,773 A | 7/1990 | Strand | |
| 4,985,037 A | 1/1991 | Petersen | |
| 4,995,883 A | 2/1991 | Demane et al. | |
| 5,002,578 A | 3/1991 | Luman | |
| 5,002,581 A | 3/1991 | Paxson et al. | |
| 5,019,108 A | 5/1991 | Bertin et al. | |
| 5,026,280 A | 6/1991 | Durr et al. | |
| 5,035,712 A | 7/1991 | Hoffman | |
| 5,058,936 A | 10/1991 | Kapgan et al. | |
| 5,080,676 A | 1/1992 | May | |
| 5,080,685 A | 1/1992 | Bolesky et al. | |
| 5,108,437 A | 4/1992 | Kenna | |
| 5,108,452 A | 4/1992 | Fallin | |
| 5,133,760 A | 7/1992 | Petersen et al. | |
| 5,133,771 A | 7/1992 | Duncan et al. | |
| 5,147,407 A | 9/1992 | Tager | |
| 5,152,796 A | 10/1992 | Slamin | |
| 5,181,928 A | 1/1993 | Bolesky et al. | |
| 5,190,549 A | 3/1993 | Miller et al. | |
| 5,194,066 A | 3/1993 | Van Zile | |
| 5,197,720 A | 3/1993 | Renz et al. | |
| 5,201,882 A | 4/1993 | Paxson | |
| 5,271,737 A | 12/1993 | Baldwin et al. | |
| 5,286,260 A | 2/1994 | Bolesky et al. | |
| 5,290,313 A | 3/1994 | Heldreth | |
| 5,314,479 A | 5/1994 | Rockwood, Jr. et al. | |
| 5,342,366 A | 8/1994 | Whiteside et al. | |
| 5,344,457 A | 9/1994 | Pilliar et al. | |
| 5,364,397 A | 11/1994 | Hayes et al. | |
| 5,370,706 A | 12/1994 | Bolesky et al. | |
| 5,397,360 A | 3/1995 | Cohen et al. | |
| 5,405,398 A | 4/1995 | Buford | |
| 5,413,605 A | 5/1995 | Ashby et al. | |
| 5,489,309 A | 2/1996 | Lackey et al. | |
| 5,489,311 A | 2/1996 | Cipolletti | |
| 5,507,817 A | 4/1996 | Craig et al. | |
| 5,507,826 A | 4/1996 | Besselink et al. | |
| 5,507,830 A | 4/1996 | Demane et al. | |
| 5,549,706 A | 8/1996 | McCarthy | |
| 5,580,247 A | 12/1996 | Gittleman | |
| 5,584,695 A | 12/1996 | Lal Sachdeva et al. | |
| 5,597,378 A | 1/1997 | Jervis | |
| 5,607,431 A | 3/1997 | Dudasik et al. | |
| 5,609,641 A | 3/1997 | Johnson et al. | |
| 5,609,645 A | 3/1997 | Vinciguerra | |
| 5,645,607 A | 7/1997 | Hickey | |
| 5,653,764 A | 8/1997 | Murphy | |
| 5,653,765 A | 8/1997 | McTighe et al. | |
| 5,658,349 A | 8/1997 | Brooks et al. | |
| 5,665,121 A | 9/1997 | Gie et al. | |
| 5,683,404 A | 11/1997 | Johnson | |
| 5,702,480 A | 12/1997 | Kroph et al. | |
| 5,702,486 A | 12/1997 | Craig et al. | |
| 5,725,592 A | 3/1998 | White et al. | |
| 5,755,720 A | 5/1998 | Mikhail | |
| 5,766,262 A | 6/1998 | Mikhail | |
| 5,766,263 A | 6/1998 | Grundei et al. | |
| 5,776,200 A | 7/1998 | Johnson et al. | |
| 5,782,921 A | 7/1998 | Colleran et al. | |
| 5,791,899 A | 8/1998 | Sachdeva et al. | |
| 5,858,020 A | 1/1999 | Johnson et al. | |
| 5,860,982 A | 1/1999 | Ro et al. | |
| 5,876,459 A | 3/1999 | Powell | |
| 5,885,295 A | 3/1999 | McDaniel et al. | |
| 5,888,206 A | 3/1999 | Lob et al. | |
| 5,888,208 A | 3/1999 | Ro | |
| 5,902,340 A | 5/1999 | White et al. | |
| 5,906,644 A | 5/1999 | Powell | |
| 5,931,871 A | 8/1999 | Baur et al. | |
| 5,944,756 A | 8/1999 | Fischetti et al. | |
| 5,954,725 A | 9/1999 | Sherman et al. | |
| 5,976,147 A | 11/1999 | LaSalle et al. | |
| 5,976,188 A | 11/1999 | Dextradeur et al. | |
| 6,048,365 A | 4/2000 | Burrows et al. | |
| 6,074,424 A | 6/2000 | Perrone, Jr. et al. | |
| 6,086,614 A | 7/2000 | Mumme | |
| 6,090,146 A | 7/2000 | Rozow, III et al. | |
| 6,099,570 A | 8/2000 | Livet et al. | |
| 6,102,956 A | 8/2000 | Kranz | |
| 6,109,602 A | 8/2000 | Schron, Jr. et al. | |
| 6,126,691 A | 10/2000 | Kasra et al. | |
| 6,136,035 A | 10/2000 | Lob et al. | |
| 6,139,584 A | 10/2000 | Ochoa et al. | |
| 6,159,217 A | 12/2000 | Robie et al. | |
| 6,165,223 A | 12/2000 | Metzger et al. | |
| 6,193,759 B1 | 2/2001 | Ro et al. | |
| 6,197,063 B1 | 3/2001 | Dews | |
| 6,203,575 B1 | 3/2001 | Farey | |
| 6,210,413 B1 | 4/2001 | Justis et al. | |
| 6,214,052 B1 | 4/2001 | Burkinshaw | |
| 6,214,053 B1 | 4/2001 | Ling et al. | |
| 6,238,435 B1 | 5/2001 | Meulink et al. | |
| 6,257,593 B1 | 7/2001 | White | |
| 6,264,699 B1 | 7/2001 | Noiles et al. | |
| 6,273,915 B1 | 8/2001 | Grimes | |
| 6,290,726 B1 | 9/2001 | Pope et al. | |
| 6,299,648 B1 | 10/2001 | Doubler et al. | |
| 6,306,172 B1 | 10/2001 | O'Neil | |
| 6,306,174 B1 | 10/2001 | Gie et al. | |
| 6,319,286 B1 | 11/2001 | Fernandez et al. | |
| 6,379,388 B1 | 4/2002 | Ensign et al. | |
| 6,436,145 B1 | 8/2002 | Miller | |
| 6,669,728 B2 | 12/2003 | Despres et al. | |
| 2002/0004685 A1 | 1/2002 | White | |
| 2002/0007220 A1 | 1/2002 | Gie et al. | |
| 2002/0059000 A1 | 5/2002 | Dwyer et al. | |
| 2002/0072799 A1 | 6/2002 | Despres, III et al. | |
| 2002/0072802 A1 | 6/2002 | O'Neil et al. | |
| 2002/0103541 A1 | 8/2002 | Meyers et al. | |
| 2003/0158606 A1 | 8/2003 | Coon et al. | |
| 2003/0204263 A1 | 10/2003 | Justin et al. | |
| 2004/0073315 A1 | 4/2004 | Justin et al. | |
| 2005/0283250 A1 | 12/2005 | Coon et al. | |
| 2005/0283251 A1 | 12/2005 | Coon et al. | |
| 2006/0195196 A1 | 8/2006 | Pendleton et al. | |
| 2007/0162145 A1 | 7/2007 | Justin et al. | |
| 2009/0187251 A1 | 7/2009 | Justin et al. | |

FOREIGN PATENT DOCUMENTS

| | | |
|---|---|---|
| DE | 3340767 A1 | 5/1985 |
| DE | 4031520 A1 | 4/1992 |
| EP | 0000549 A1 | 2/1979 |
| EP | 0201407 A1 | 11/1986 |
| EP | 0283706 A1 | 9/1988 |
| EP | 0336774 A1 | 10/1989 |
| EP | 0336774 B1 | 10/1989 |
| EP | 0359457 A1 | 3/1990 |
| EP | 0376658 A2 | 7/1990 |
| EP | 0433121 A1 | 6/1991 |
| EP | 0495340 A1 | 7/1992 |
| EP | 0556997 A1 | 8/1993 |
| EP | 0552950 B1 | 9/1996 |
| EP | 0832620 A2 | 4/1998 |
| EP | 0878177 A2 | 11/1998 |
| EP | 0913132 A1 | 5/1999 |
| EP | 0714645 B1 | 5/2000 |
| EP | 1004283 A2 | 5/2000 |
| EP | 1132064 A2 | 9/2001 |

| | | | |
|---|---|---|---|
| EP | 0956836 B1 | 7/2004 |
| EP | 1449500 A2 | 8/2004 |
| EP | 1059070 B1 | 4/2005 |
| FR | 2225141 A1 | 11/1974 |
| FR | 2705558 A1 | 12/1994 |
| FR | 2748389A1 | 11/1997 |
| FR | 2799115 A1 | 4/2001 |
| GB | 1472311 A | 5/1977 |
| JP | 10-513079 A | 12/1998 |
| JP | 10-513079 T | 12/1998 |
| JP | 2001-087292 A | 4/2001 |
| WO | WO83/02555 A1 | 8/1983 |
| WO | WO85/03426 A1 | 8/1985 |
| WO | WO86/02260 A1 | 4/1986 |
| WO | WO86/06954 A1 | 12/1986 |
| WO | WO91/17723 A1 | 11/1991 |
| WO | WO91/18563 A1 | 12/1991 |
| WO | WO96/13233 A1 | 5/1996 |
| WO | WO9623459 A1 | 8/1996 |
| WO | WO97/20525 A1 | 6/1997 |
| WO | WO98/08467 A1 | 3/1998 |
| WO | WO98/08468 A1 | 3/1998 |
| WO | WO00/72784 A1 | 12/2000 |
| WO | WO02/07647 A2 | 1/2002 |
| WO | WO03/070127 A1 | 8/2003 |

OTHER PUBLICATIONS

The Response filed Mar. 25, 2009 to the Office Action mailed Oct. 16, 2008 in related Australian application No. 2004200394.
The European Search Report completed Aug. 12, 2004 and published Oct. 20, 2004 in related European application No. 04250511.5.
The Office Action mailed Jan. 31, 2005 in related European application No. 04250511.5.
The Office Action mailed Feb. 11, 2005 in related European application No. 04250511.5.
The Response filed Jun. 9, 2005 to the Office Action mailed Feb. 11, 2005 in related European application No. 04250511.5.
Japanese Office Action mailed Apr. 5, 2011 in related Japanese Application No. 2004-295021 and its English translation.
European Search Report mailed Dec. 17, 2010 in related European application No. 10179328.9.

MODULAR BONE IMPLANT, TOOL, AND METHOD

CROSS REFERENCE TO RELATED APPLICATION

This application is a continuation of U.S. patent application Ser. No. 11/625,053, filed Jan. 19, 2007, now U.S. Pat. No. 7,857,858, which is a continuation of U.S. patent application Ser. No. 10/369,331, filed Feb. 18, 2003, now U.S. Pat. No. 7,182,786, which is a continuation-in-part of U.S. patent application Ser. No. 10/132,668, filed on Apr. 25, 2002, now abandoned, the disclosures of which are hereby expressly incorporated by reference herein in their entireties.

BACKGROUND

Field of the Invention

The present invention relates to modular bone implants, means of assembly, and their method of use.

SUMMARY

Modular bone implants, means of assembly, and their method of use are presented.

In one form thereof, the present disclosure provides a tibial component of a knee prosthesis comprising a tray having substantially planar top and bottom surfaces and an extension forming an elongate body having a top end and a bottom end, one of the tray and extension including an outwardly projecting boss, the boss having an outer wall including a cylindrical portion and a tapered portion, the other of the tray and extension including an inwardly extending bore forming a bore wall, the bore wall including a cylindrical portion and a tapered portion, the extension being removably engagable with the tray with the boss received in the bore, the tapered portion of the boss seating on the tapered portion of the bore and the cylindrical portion of the boss being received by the cylindrical portion of the bore in press-fit relationship to form a junction between the tray and extension.

In another form thereof, the present disclosure provides a bone joint implant comprising: a first component having top and bottom surfaces; and a second component having a top end and a bottom end and an axis from the top end to the bottom end, the second component being removably affixed to the bottom of the first component, one of the first and second components including a male junction element having an outer wall including a first seating portion having a first shape and a second seating portion having a second shape, the other of the first and second components including a female junction having an inner wall including a first seating portion having a first shape congruent with the male first seating portion shape and a second seating portion having a second shape congruent with the male second seating portion shape, the first and second seating portion shapes being incongruent, the second component being releasably joined with the first component with the male first and second seating portions being in close fitting relationship with the female first and second seating portions.

In yet another form thereof, the present disclosure provides a tibial component of a knee prosthesis comprising: a tray having top and bottom surfaces; and a keel having a top end and a bottom end and an axis from the top end to the bottom end, the keel being engagable with the bottom of the tray, the keel and tray forming a junction including a rotational alignment means for aligning the keel and tray in a predetermined relationship for assembly, the alignment means being sealed within the junction to prevent migration of material from the rotational alignment means outside of the junction.

In still another form thereof, the present disclosure provides a tool for assembling first and second modular joint components, the tool comprising first and second tool elements connectable to the first and second joint components respectively, the tool containing stored energy able to bias the first and second tool elements relative to one another upon activation of the tool to draw the first and second modular joint components into seating relationship.

In a further form thereof, the present disclosure provides a tool for assembling first and second modular joint components, the tool comprising a handle; a first shaft member mounted on the handle for axial translation and being engagable with the first joint component in axial force transmitting relationship; a second shaft member fixed to the handle and being engagable with the second joint component in axial force transmitting relationship; a motor engaging the first member to impart axial force to the first member to move the joint components into engagement, the tool storing energy to drive the motor.

In one form thereof, the present disclosure provides a method for assembling a modular joint component, the method comprising the steps of providing first and second modular joint components having corresponding first and second engagement portions; providing a tool having first and second tool elements, the tool containing stored energy able to bias the first and second tool elements relative to one another; aligning the first and second engagement portions; engaging the tool first and second tool elements with the first and second joint components, activating the tool to release the stored energy to bias the first and second tool elements and draw the first and second joint components together.

In another form thereof, the present disclosure provides a method for implanting a modular tibial component into a knee, the method comprising the steps of providing separate, modular tibial tray and keel components; forming an incision in the knee joint; preparing the tibial bone to receive the components; inserting the keel component through the incision and seating it in the prepared tibial bone; inserting the tray component through the incision and assembling it to the keel component in situ; and closing the incision.

BRIEF DESCRIPTION OF THE DRAWINGS

The above-mentioned and other features of this disclosure, and the manner of attaining them, will become more apparent and will be better understood by reference to the following description of embodiments of the disclosure taken in conjunction with the accompanying drawings, wherein.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 1:
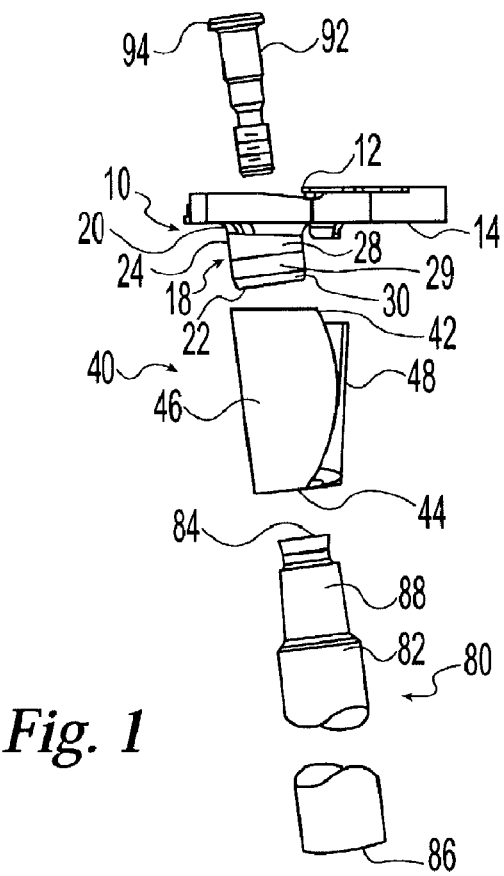
FIG. 1 is an exploded side elevation view of an illustrative embodiment of a bone implant according to the present invention.
Figure 2:
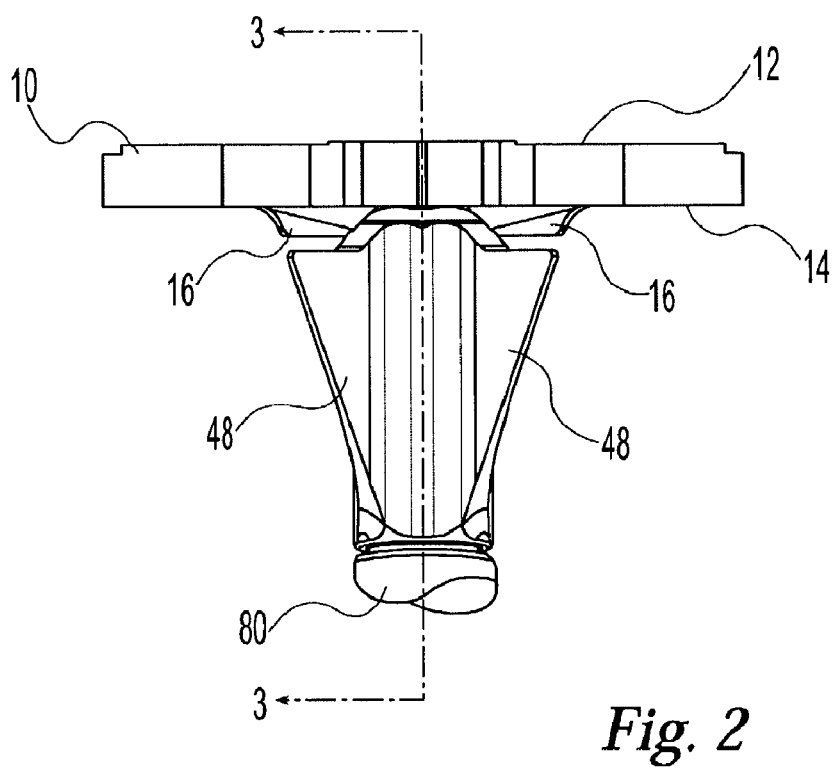
FIG. 2 is a rear elevation view of the illustrative embodiment of FIG. 1.
Figure 3:
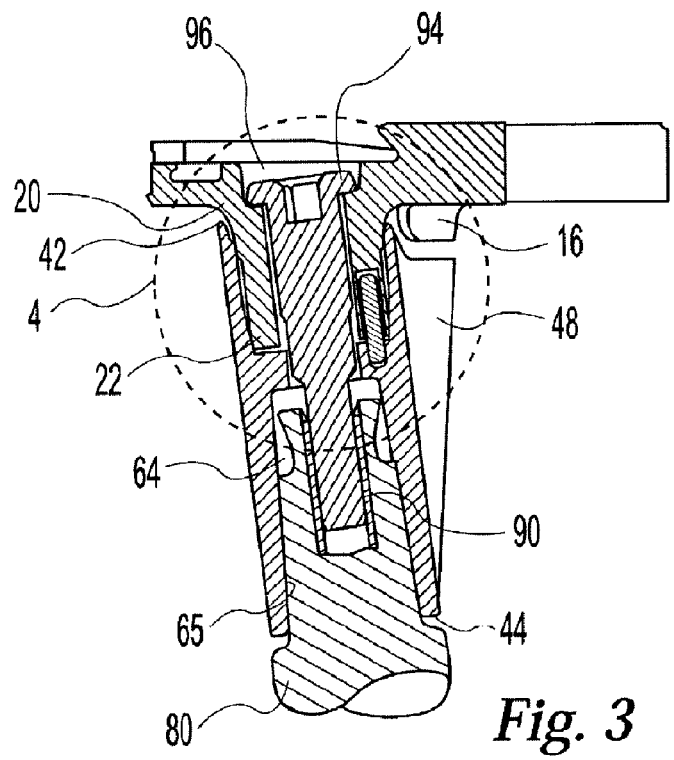
FIG. 3 is a side sectional view of the illustrative embodiment of FIG. 1 taken along line 3-3 of FIG. 2.

The present invention is applicable to any bone implant in which modularity is advantageous. Examples include joint prostheses for the knee, hip, shoulder, elbow, ankle, and wrist. Such prostheses are implanted by first making an incision near the joint to access the joint space, cutting away the articulating bone ends to be replaced, and seating the prostheses on the cut bone ends. FIGS. 1-6 depict an illustrative tibial knee prosthesis used to describe the various aspects of the invention.

A tibial prosthesis 2 includes separate tray 10, keel 40, and stem 80 components able to be joined together to form a desired joint prosthesis configuration for replacing the articular surface of the proximal tibia. The tray 10 includes generally planar top 12 and bottom 14 surfaces. The top surface 12 is configured to receive a bearing surface (not shown), such as a polyethylene bearing surface, as is known in the art. The bottom surface 14 is configured to sit on the cut end of the proximal tibia. One or more fins 16 extend radially along the bottom surface and project downwardly from the bottom surface. The fins 16 are received in grooves cut in the proximal tibia to provide rotational resistance to the prosthesis. The fins 16 also serve to strengthen the tray 10 by increasing the bending moment of inertia of the tray. Where further stability is desired, the tray provides for the modular attachment of additional components via a boss 18 extending downwardly from the bottom surface 14. The boss 18 includes a top end 20 joined to the bottom surface 14 of the tray 10, a freely projecting bottom end 22, and an axis extending from the top end 20 to the bottom end 22. An outer wall 24 defines the exterior of the boss 18 and an inner bore 26 extends from the top end 20 to the bottom end 22. The outer wall includes a cylindrical mating portion 28, a tapered mating portion 30, and a relieved, non-mating portion 29 therebetween. An alignment hole 32 is formed in the bottom end 22 and extends upwardly between the outer wall 24 and the inner bore 26. The fins 16 can attach to the boss 18, or they can stop short of the boss 18 to leave a gap 34.

An extension can be mounted on the tray to increase the stability of the tibial prosthesis on the bone. Such an extension can take the form of a stem, a fluted stem, or a keel. The extension can be symmetric or asymmetric. In the illustrative embodiment, a keel 40 is mated to the boss 18 to increase both the rotational and bending stability of the tibial prosthesis on the bone. The keel 40 includes an elongate body having a top end 42 and a bottom end 44 with an axis extending between them, and an outer wall 46. The keel includes at least one fin 48 extending axially along the outer surface 46 and projecting radially outwardly. The keel includes a first axial bore 50 extending downwardly from the top end 42 and having a bore wall including a cylindrical mating portion 52, a tapered mating portion 54, and an end wall 56. An alignment hole 58 is formed in the end wall 56 and extends downwardly. The keel further includes a second axial bore 64 extending upwardly from the bottom end 44 and comprising a tapered side wall 65. A keyed portal 66 communicates between the first 50 and second 64 axial bores. The portal 66 includes a circular central opening 67 and side slots 68 forming a bayonet engagable member.

Alternately, the portal 66 can be threaded for engaging a threaded member.

Figure 4:
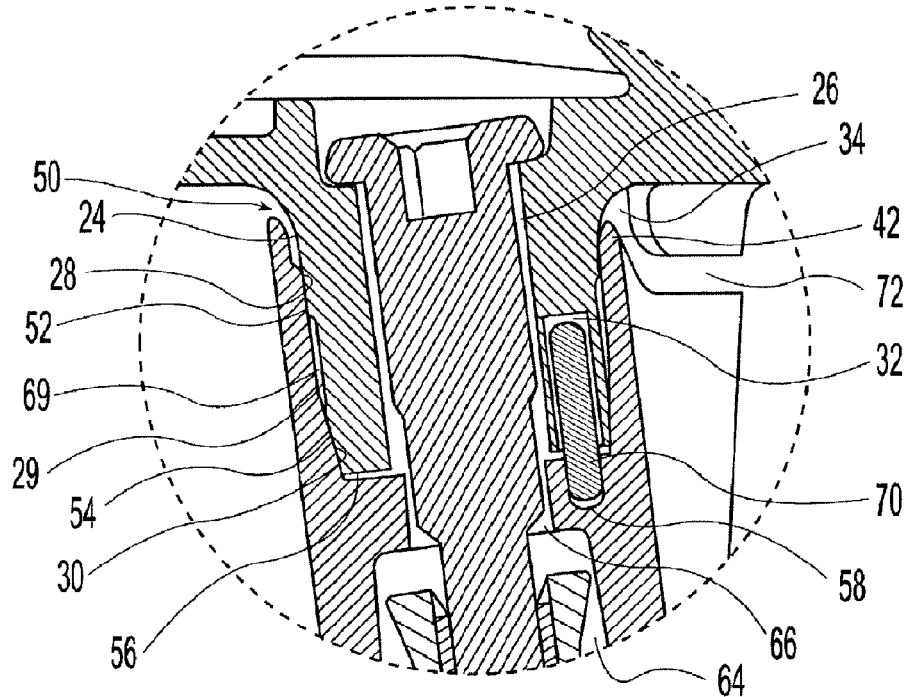
FIG. 4 is a detail view of the sectional view of FIG. 3.
Figure 5:
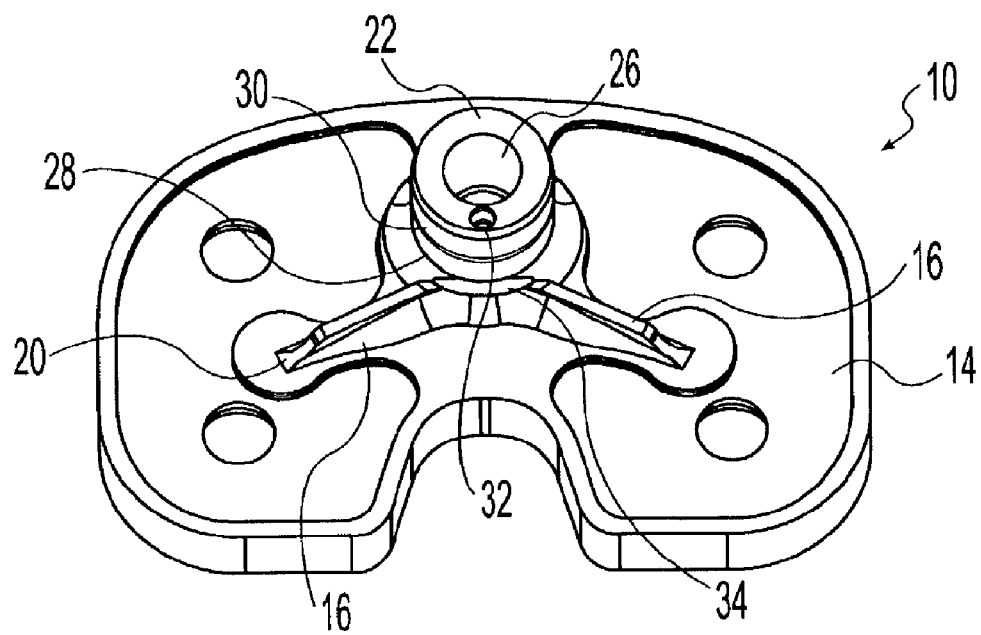
FIG. 5 is a bottom perspective view of the tray of the illustrative embodiment of FIG. 1.

The keel 40 engages the tray 10 with the boss 18 received in the first axial bore 50, the tapered portion 30 of the boss seating on the tapered portion of the bore 54, and the cylindrical portion 28 of the boss being received by the cylindrical portion 52 of the bore in press-fit relationship to form a junction between the tray 10 and keel 40. The tapered portions aid in aligning the components as they are brought together. The cylindrical press-fit locks the components together. The cylindrical press-fit also provides a fluid tight seal to prevent material from migrating past the press-fit into or out of the junction. In the illustrative embodiment, the relieved portion 29 of the boss results in a circumferential gap 69 between the boss 18 and first axial bore 50 lying between the cylindrical 28, 52 and tapered 30, 54 portions of the junction. The tray 10 and keel 40 can be aligned by providing an alignment pin 70 in one of the alignment holes 32, 58. In the illustrative embodiment, the keel alignment hole is slightly smaller than the pin 70 and the pin 70 is pressed into it. The tray alignment hole 32 is slightly larger than the pin. As the components are brought together, they are prevented from seating until the tray alignment hole 32 engages the pin 70. Where a gap 34 exists between the boss 18 and fins 16, the top end 42 of the keel 40 can extend further up and fit into the gap 34 as shown in FIG. 4.

The junction of the present invention makes use of a press-fit which is advantageous over Morse taper-type arrangements used alone. The press fit allows the components to slide together in tight frictional engagement to create a fluid-tight seal and strong resistance to dislocation. The practicalities of machining result in a press-fit having a band, or area, of contact whereas a taper typically has line contact between the mating parts. The press-fit therefore provides a better seal and is more likely to prevent material from migrating across the press-fit boundary. Furthermore, the press-fit locking arrangement is not dependent on precise axial positioning between the components and therefore allows them to be positioned axially at a desired location, once initial press-fit engagement has been achieved. While a cylindrical press fit has been shown and lends itself to precise manufacturing, other cross-sectional shapes can be used in a sliding press-fit according to the invention. The junction also utilizes a taper engagement which provides for centering of the components during assembly and a positive stop to seating as the tapered portions bottom on one another. When the taper is fully seated, it provides increased bending strength to the junction due to the axial distance between the press fit and taper contacts. As shown in FIG. 4, the press-fit 28, 52 and tapered 30, 54 portions are spaced apart axially as far as possible to maximize the bending strength of the junction. The illustrative taper is greater than 3° to facilitate manufacturing of a taper with a predictable seating depth. However, the taper can be a locking taper to provide further locking strength. Because the press-fit permits continued axial translation during assembly after it is engaged, the tapered portion of the junction can be locked after the press-fit has been engaged. A locking taper would be on the order of 1.5-3°.

Figure 6:
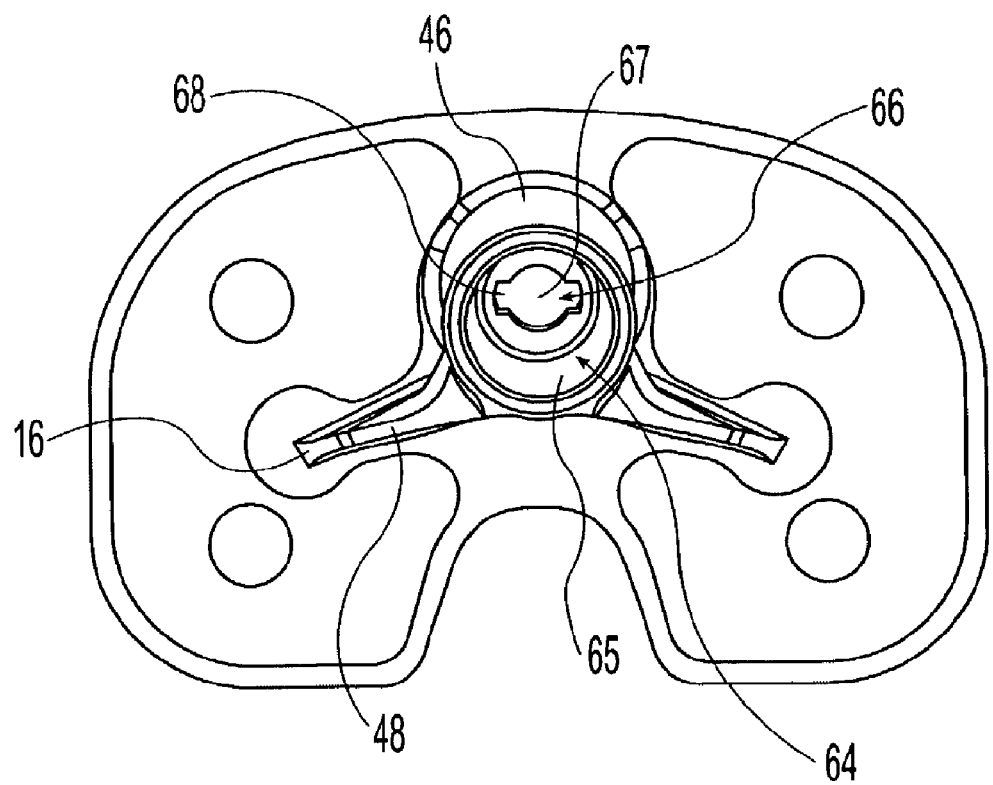
FIG. 6 is a bottom plan view of the tray and keel of the illustrative embodiment of FIG. 1 assembled together.
Figure 7:
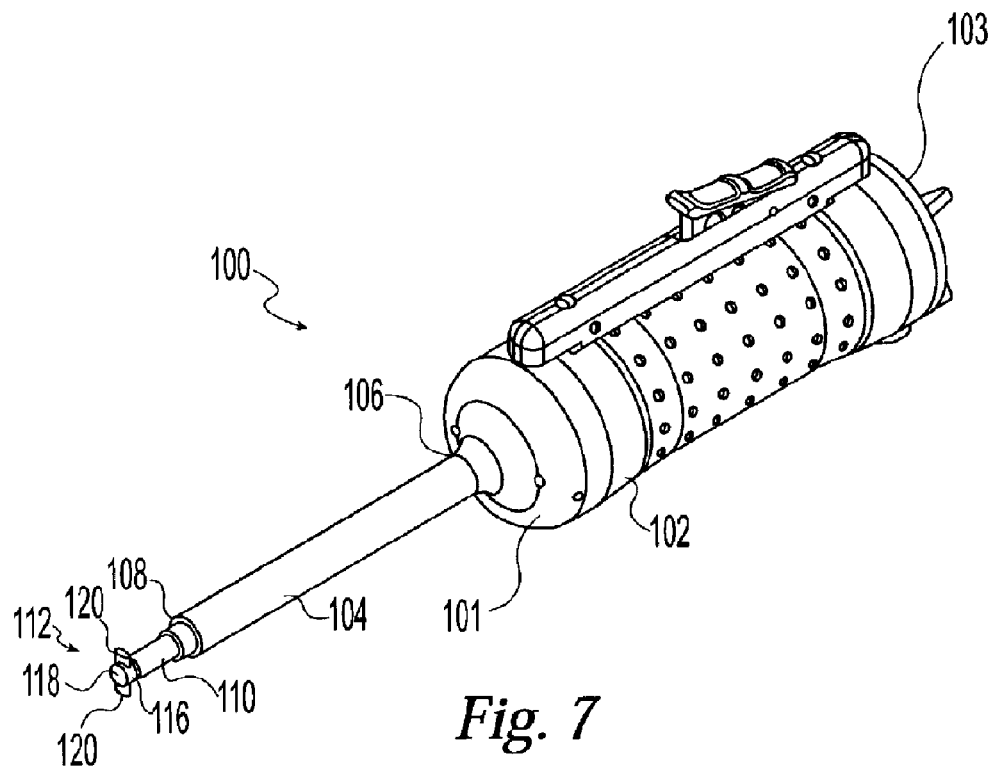
FIG. 7 is a perspective view of an illustrative embodiment of an assembly tool according to the present invention.
Figure 8:
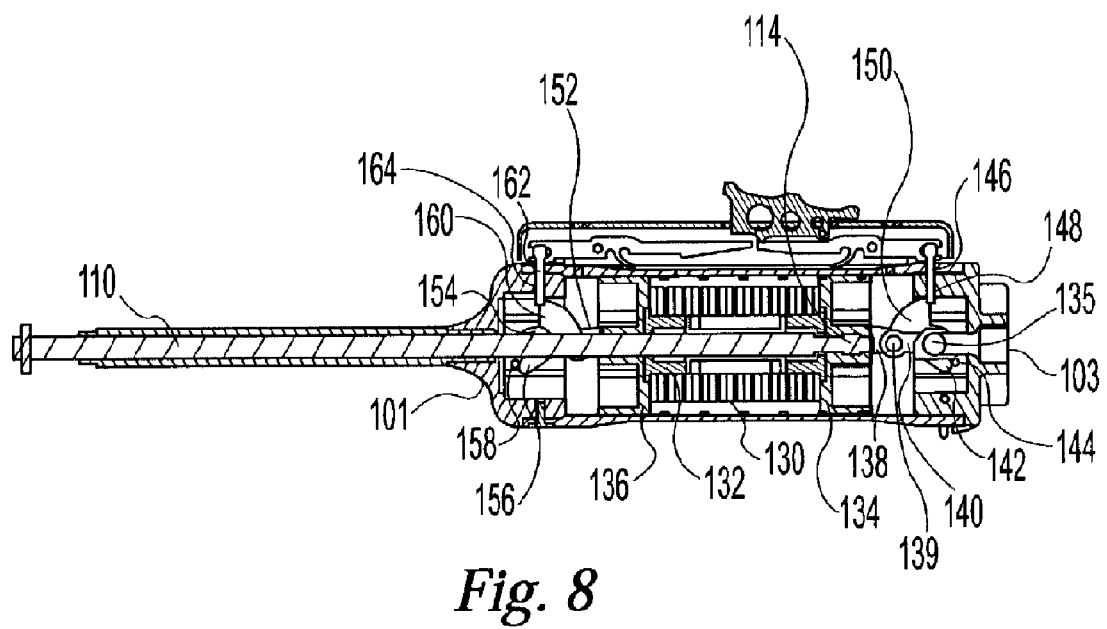
FIG. 8 is a side sectional view of the illustrative embodiment of FIG. 7 showing the assembly tool in a condition ready for use.
Figure 9:
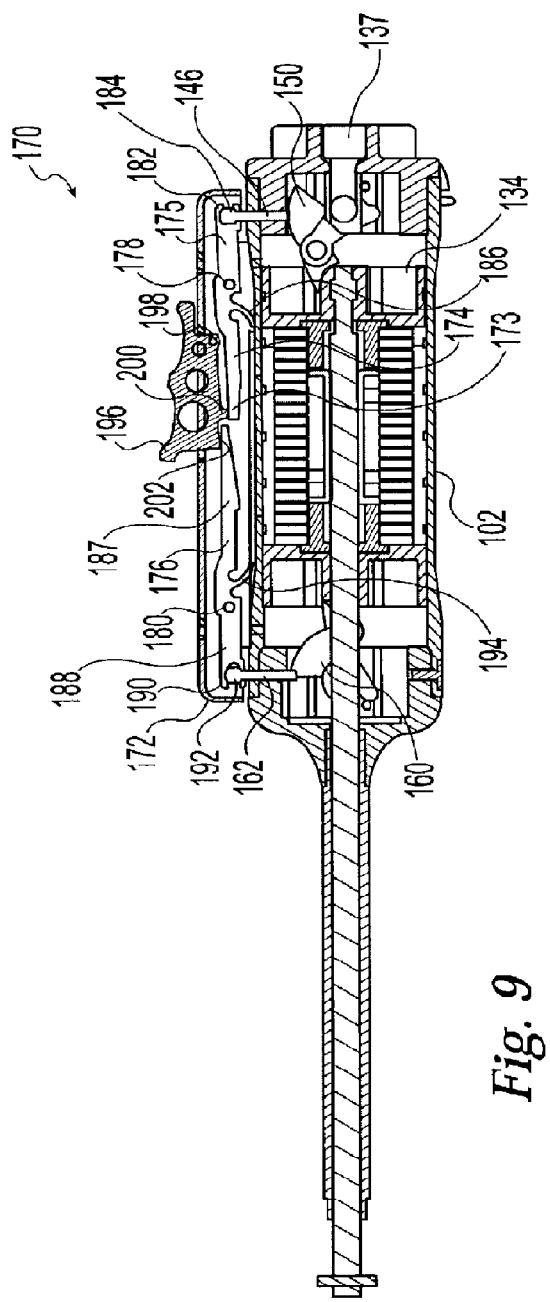
FIG. 9 is a side sectional view of the illustrative embodiment of FIG. 7 showing the assembly tool after the first stage of its two stage activation.
Figure 10:
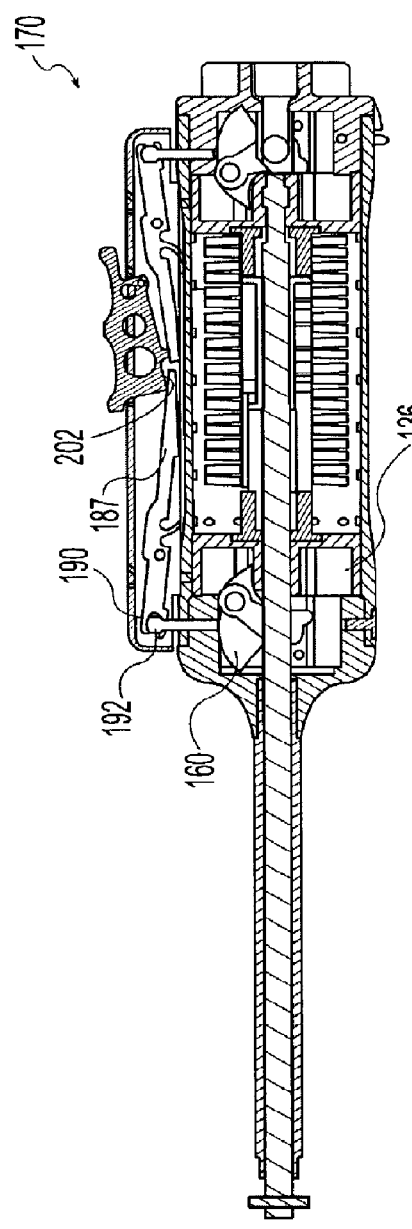
FIG. 10 is a side sectional view of the illustrative embodiment of FIG. 7 showing the assembly tool during the second stage of its two stage activation.

When assembled, the tray 16 and keel 48 fins are generally aligned with one another from top to bottom to project as a single fin, as best seen in FIG. 6. However, when the tray and keel are fully assembled, there remains an axial gap 72 between the fins 16, 48 so that they do not touch. In the illustrative embodiment, the first axial bore is arranged with the cylindrical press fit portion 52 above the tapered portion 54 and locking pin 70. With this arrangement, and the axial spacing 72 of the fins 16, 48, there is no contact between the tray 10 and keel 40 outside of the junction. Any particles that may be produced by contact between the components are sealed in the junction so that they cannot migrate upward into the joint space. While it is within the scope of the invention to form the tapered portions above the cylindrical portions to provide the centering and locking functions, such an arrangement does not provide the same sealing characteristics.

A stem 80 can be combined with the tray 10 and keel 40 assembly to provide further bending stability to the tibial prosthesis. The stem 80 includes a shaft 82 having a top end 84 and a bottom end 86. The top end 84 includes a tapered portion 88 and an axial threaded bore 90. The tapered portion 88 of the stem is received in the second axial bore 64 of the keel 40. This taper joint can also be provided as a self locking taper. A bolt 92 extends through the inner bore 26 of the boss and the portal 66 and threads into the threaded bore 90 of the stem to draw and hold the components together. The head 94 of the bolt is recessed into a counter bore 96 formed in the top surface 12 of the tray.

The invention further comprises an assembly tool for assembling modular joint components requiring a linear biasing force during assembly. The assembly tool is particularly well suited where high assembly forces are required. It is also well suited for a minimally invasive approach to the joint where an assembly force needs to be delivered to a small remote surgical space. The press-fit arrangement of the illustrative modular implant embodiment requires from 1000 to 2000 pounds of assembly force depending on the amount of interference between the press-fit components. For example, a 0.001 inch interference has been found to require 1000 pounds and a 0.002 inch interference has been found to require 2000 pounds. Likewise, when the components are positioned for assembly, it has been found that 0.050 inches of displacement are required to remove slack from the assembly and another 0.100 inches of displacement to fully engage the components.

FIGS. 7-10 depict an illustrative embodiment of an assembly tool capable of providing the force and displacement required for assembling the illustrative modular implant. A compressor 100 includes a handle 102 having proximal 101 and distal 103 ends, a first shaft member 104 having a mounting end 106 rigidly attached to the handle and a working end 108, and a second shaft member 110 coaxially mounted within the first shaft member for axial translation relative to the first shaft member 104. The second shaft member includes a first end 112 and a second end 114. The first end 112 includes an engagement tip 116 such as a threaded tip or a bayonet tip. The illustrative embodiment comprises a T-shaped bayonet tip 116 having a round central portion 118 and a pair of ears 120 extending radially outwardly. The bayonet tip 116 is generally the same shape as the portal 66 in the keel 40 and can be attached to the keel by inserting it into the portal 66 and rotating the second shaft member 110 one-quarter turn relative to the keel so that the ears 120 extend beyond and grip the underside of the portal 66. A linear motor is located inside the handle 102 and is connected to the second end 114 of the second shaft member 110 in axial force transmitting relation. The motor stores energy until it is needed to assemble the modular joint components. When activated, the motor causes the second shaft member 110 to translate toward the handle and thus the bayonet 116 tip to move toward the working end 108 of the first shaft member 104.

In use, the modular joint components are initially engaged with the boss 18 received within the axial bore 50. The first 104 and second 110 shaft members are inserted along the inner bore 26 until the bayonet tip 116 of the second shaft member 110 extends through the portal 66. The tool is rotated so that the ears 120 extend underneath the edges of the portal 66. At this point, the bayonet tip 116 positively engages the keel 40 and the working end 108 of the first shaft member 104 rests against the bottom of the counter bore 96. The motor is actuated and the second shaft is withdrawn to draw the tray 10 and keel 40 into locking engagement. The tool 100 is then rotated until the ears 120 again align with the portal 66 and the tool is withdrawn.

A variety of motor mechanisms can be provided to generate the linear motion to operate the tool 100. Examples include electric and pneumatic rotary motors coupled with rotary-to-linear transmissions, linear pneumatic pistons, and spring mechanisms. The illustrative embodiment depicts a linear spring motor comprising twenty Belleville washers 130 constrained by a telescoping core 132. First 134 and second 136 motion blocks abut opposite ends of the stack of washers 130. Absent other constraints, the first and second motion blocks 134, 136 and washers 130 are free to translate axially within the handle 102. The second shaft member 110 extends through the second motion block 136 and telescoping core in axial sliding relationship. The second end 114 of the second shaft member 110 is coupled to the first motion block 134 such that the second shaft member 110 moves with the first motion block 134. An axial opening 137 communicates from the exterior to the interior of the handle in alignment with the first motion block 134. The opening 137 permits a ram attached to an external press to be inserted into the handle 102 to press against the first motion block 134 to compress the mechanism.

A linkage comprising a pair of links is positioned at each end of the handle to provide positive capture and release of the two motion blocks. The distal linkage comprises a first link 138 and a second link 140 pinned together 139 for rotation relative to one another. The first link is pinned at its opposite end to the first motion block 134 for rotation relative to the first motion block 134. The second link is pinned 135 at its opposite end to the distal end 103 of the handle for rotation relative to the handle. The linkage is prevented from aligning at the point of singularity along its pivot axes, or top dead center, by a tang 142 projecting from the second link 140 to contact a pin 144 in the handle. The tang 142 and pin 144 stop counter clockwise rotation of the linkage 2° before reaching the point of singularity. A first locking pin 146 slides in a bore 148 in the side of the handle 102 to engage a cam 150 on the second link 140 to releasably block the linkage from rotating clockwise. Due to the shallow angle of the linkage in this position, large axial forces on the motion block impart relatively small forces against the locking pin 146. A similar linkage comprising a pair of links 152, 154 is pinned to the proximal end 101 of the housing and second motion block 136. This linkage is similarly restrained against over rotation by a tang 156 and pin 158 and is releasably blocked by a second locking pin 162 sliding in a bore 164.

A trigger mechanism 170 is provided to simplify the sequential operation of the two locking pins 146, 162. A trigger housing 172 is mounted on the handle 102 and supports the other parts of the mechanism. A first lever 174 is pinned 178 for rotation in the housing 172 and includes an input end 173 and an output end 175. The output end 175 is connected to the first locking pin 146 via a yoke 182 surrounding a ball end 184 formed on the locking pin 146. The input end 173 of the first lever 174 is biased upwardly by a leaf spring 186, thereby biasing the locking pin 146 downwardly into engagement with the cam 150. The first lever pivot pin 178 is nearer the output end 175 so that there is a mechanical advantage proportional to the ratio of the input and output lengths. Therefore, forces applied at the input end 173 are multiplied to ease manipulation of the locking pin 146. Similarly, the second lever 176 is pinned 180 for rotation in the housing 172 and includes an input end 187 and an output end 188. The output end 188 is connected to the second locking pin 162 via a yoke 190 surrounding a ball end 192 formed on the locking pin 162. The input end 187 of the second lever 176 is biased upwardly by a leaf spring 194, thereby biasing the locking pin 162 downwardly into engagement with the cam 160. A trigger 196 is pinned 198 for rotation in the trigger housing 172 and overlies the input ends 173, 187 of the two levers 174, 176. The trigger 196 includes a first contact 200 projecting downwardly to engage the input end 173 of the first lever 174. The trigger 196 includes a second contact 202 projecting downwardly to engage the input end 187 end of the second lever 176. The second contact 202 is spaced, relative to the first contact 200, so that it does not activate the second lever 176 until after the first lever 174 has been fully activated.

In use, the assembly tool 100 is held with its distal end down so that gravity moves the second motion block 136 axially downwardly toward the center of the mechanism. As the second motion block 136 moves, the proximal linkage rotates clockwise with the end of the second locking pin 162 riding on the cam 160. When the linkage is straightened to its limits, the locking pin 162 slips over the end of the cam 160 and snaps into position to lock the second motion block 136. The first motion block 134 is now axially pressed toward the center of the mechanism with an external press to compress the washers 130. As the first motion block 134 moves, the distal linkage rotates counterclockwise with the end of the first locking pin 146 riding on the cam 150. When the linkage is straightened to its limits, the pin 146 slips over the end of the cam 150 and snaps into position to lock the first motion block 134. The precharged assembly tool is now in condition to be used to assemble the modular joint components. The tool 100 is engaged with the implant components. The trigger 196 is pressed to activate the tool. As the trigger 196 rotates about its pivot pin 198, the first contact 200 presses the input end 173 of the first lever 174 causing the output end 175 to withdraw the first locking pin 146 and release the distal linkage. The distal linkage rotates clockwise and permits the first motion block 134 to spring distally. The second shaft member 110 moves with the first motion block 134 and draws the modular components together. The spring action of the tool snaps the press-fit junction into engagement. With the first motion block 134 released, the remaining spring tension still exceeds the minimum required to seat the press-fit junction. This ensures that the junction is fully seated but makes it difficult to disengage the tool 100 from the joint components. Therefore, continued pressing of the trigger causes the second contact 202 to press against the input end 187 of the second lever 176 to withdraw the second locking pin 162. This permits the second motion block 136 to spring proximally and release the remaining spring tension. The tool 100 can now be disengaged from the joint components. The two stage trigger release happens quickly and is transparent to the user who is simply required to fully depress the trigger once to cause the separate sequential releases.

In clinical use, an incision is made in the knee joint. For a minimally invasive surgical approach according to the present invention, an incision is made on one of the medial and lateral sides of the knee joint to expose the joint surfaces while avoiding compromising the soft tissue of the suprapatellar pouch. Next, resection instruments are introduced through the incision to prepare the proximal tibial bone and form a keel receiving recess. Ideally, only the minimum amount of bone required to provide a stable flat surface on the tibia is removed. The illustrative modular tibial component has a low profile. Because of this low profile and modularity, the incision can be quite small and need only be large enough to allow passage of the individual components. The present investigators have found that a tray component having an overall height less than 1 8 mm can be inserted through such a minimally invasive surgical incision and engage the tibia where the minimum amount of bone has been removed. The keel component of the present invention can be manipulated into the prepared joint space because it lacks the large top surface of the tray. Likewise, the low profile and modularity of the components permit the patella to remain in its anatomic orientation relative to the femur to further reduce the trauma experienced by the joint during surgery and aid recovery and ultimate outcome from the procedure. The keel is manipulated through the incision and placed into the recess. The tray is then manipulated through the incision and engaged with the keel. The assembly instrument is engaged with the tray and keel and activated to draw the components together to engage the press-fit and seat the tapered portions of the modular junction.

It will be understood by those skilled in the art that the foregoing has described illustrative embodiments of the present invention and that variations may be made to these embodiments without departing from the spirit and scope of the invention defined by the appended claims. The various aspects of the present invention are applicable to a variety of bone implants in addition to the illustrative tibial implant. Likewise, where male/female engaging portions have been depicted, the male and female components may be reversed and still be within the anticipated scope of the invention. Likewise the arrangement of the multiple incongruous junction shapes can be changed while keeping within the invention. For example, the illustrative embodiment depicts a junction including a press-fit and then a taper. The invention contemplates reversing that order so that the taper comes before the press-fit.

What is claimed is:

1. A tibial component of a knee prosthesis, comprising:
    a tibial tray having substantially planar top and bottom surfaces and an axis extending between said surfaces, at least one fin extending radially outwardly along the bottom surface and projecting axially downwardly, the tray further including an outwardly projecting boss extending from the bottom surface, the boss having an outer wall including a cylindrical portion and a tapered portion and an inner wall defining a throughbore;
    a tibial keel forming an elongate body having a top end, a bottom end, an outer surface, and an axis from the top end to the bottom end generally parallel to the tray axis, at least one fin extending axially along the outer surface and projecting radially outwardly, the tray and keel fins being generally axially aligned with one another from top to bottom to project as a single fin, the tibial keel further including a first axial bore extending inwardly from said top end and forming a bore wall, the bore wall including a cylindrical portion and a tapered portion, the tibial keel being removably engageable with the tibial tray with the boss received in the first axial bore of the tibial keel, the tapered portion of the boss seating on the tapered portion of the first axial bore to define a first junction between the tibial tray and the tibial keel, and the cylindrical portion of the boss being received by the cylindrical portion of the first bore in press-fit relationship to form a second junction between the tibial tray and tibial keel, wherein at least one of the first and second junctions includes a rotational alignment means for aligning the tibial tray and the tibial keel in a predetermined relationship for assembly, the alignment means being formed within the junction.

2. The tibial component of claim 1 wherein the tapered portions form a locking taper.

3. The tibial component of claim 1 wherein the rotational alignment means is positioned within the junction relative to the cylindrical press-fit portion so that it is sealed within the junction to prevent migration of material from the rotational alignment means outside of the junction.

4. The tibial component of claim 1 wherein the rotational alignment means comprises a pin received in a hole.

5. The tibial component of claim 4 wherein the pin is located in the first axial bore and the pin is received by a hole formed in the boss.

6. The tibial component of claim 1 wherein the tibial keel includes a second axial bore extending from the bottom end toward the top end to communicate with the first axial bore, the second axial bore forming a tapered inner wall for receiving a stem extension.

7. The tibial component of claim 6 wherein the tray includes a bore extending from the top surface downwardly through the boss in communication with the first axial bore, the tray bore receiving a bolt in engagement with one of the keel and stem extension.

8. The tibial component of claim 1 wherein one of the first and second junctions comprise a sealing junction to prevent the passage of material across the junction.

9. The tibial component of claim 1 wherein the cylindrical press-fit second junction seals a space adjacent the taper first junction to prevent the outward migration of material from the taper first junction.

10. The tibial component of claim 1 wherein the tapered portion of the boss is formed below the cylindrical portion of the boss and the tapered portion of the first axial bore is formed below the cylindrical portion of the first axial bore so that the tapered seating portion of the first junction is below the cylindrical press-fit portion of the second junction.

11. The tibial component of claim 10 wherein the cylindrical press-fit between the boss and first axial bore seals the first axial bore to prevent material from entering or leaving the portion of the first axial bore below the press-fit.

12. The tibial component of claim 1 wherein the tray and keel fins are in an axial spaced relationship so that they do not contact.

* * * * *